US00PP15207P2

(12) United States Plant Patent
McNaughton

(10) Patent No.: US PP15,207 P2
(45) Date of Patent: Oct. 5, 2004

(54) ***LAVANDULA* PLANT NAMED 'LAVSTS 154'**

(50) Latin Name: *Lavandula stoechas*
Varietal Denomination: Lavsts 154

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 0 days.

(21) Appl. No.: 10/663,850

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—S B McCormick-Ewoldt

(57) ABSTRACT

A new cultivar of *Lavandula* plant named 'Lavsts 154' that is characterized by upright bushy habit, flower spikes with vibrant pink-violet sterile bracts, and light green foliage. These traits set it apart from all other existing varieties of Lavandula known to the inventor.

3 Drawing Sheets

Genus: Lavandula.
Species: *stoechas.*
Denomination: Lavsts 154.

BACKGROUND OF THE INVENTION

The present invention relates to a new and distinct cultivar of lavender known botanically as *Lavandula stoechas* subsp. *luisieri* and hereinafter referred to by the cultivar name 'Lavsts 154'. The new invention 'Lavsts 154' is a branch sport off *Lavandula stoechas* subsp. *luisieri* 'Tickled Pink' (unpatented) and was discovered in a cultivated area of Christchurch, New Zealand by the inventor in 1999. The sport will be known as 'Lavsts 154'. The parent plant is *Lavandula stoechas* subsp. luisieri 'Tickled Pink'.

The new lavender plant 'Lavsts 154' was selected for distinct and unique traits, namely color and number of sterile bracts and floriferous nature. The closest comparison plant is the parent plant *Lavandula stoechas* subsp. luisieri 'Tickled Pink'. The new variety 'Lavsts 154' is distinguishable from the parent plant by the number of sterile bracts. 'Lavsts 154' exhibits 5–6 sterile bracts per spike, whereas the parent 'Tickled Pink' exhibits 4–5 sterile bracts per spike. 'Lavsts 154' is mainly distinguishable from all other *Lavandula stoechas* cultivars known to the inventor by its very upright, bushy growth habit. Lavsts 154 also exhibits larger and more vibrant pink-violet colored sterile bracts than other known cultivars of *Lavandula stoechas,* except for the parent, 'Tickled Pink' which has a lesser number of sterile bracts per spike. The new invention was asexually propagated by the inventor in Christchurch, New Zealand in 1999 using soft to semi-hardwood cuttings. Since that time subsequent generations have been determined fixed, stable and true to type.

SUMMARY OF THE INVENTION

The following traits have been repeatedly observed and represent the distinguishing characteristics of the new lavender cultivar 'Lavsts 154'. These traits in combination distinguish 'Lavsts 154' from all other existing varieties of *Lavandula* known to the inventor. 'Lavsts 154' has not been tested under all possible conditions and phenotypic differences may be observed with variations in environmental, climatic, and cultural conditions, however, without any variance in genotype.

1. *Lavandula* 'Lavsts 154' exhibits an upright, bushy habit.
2. *Lavandula* 'Lavsts 154' exhibits large, broad, vibrant pink-violet sterile bracts.
3. *Lavandula* 'Lavsts 154' exhibits short peduncles causing the flower spikes to sit close to the foliage.
4. *Lavandula* 'Lavsts 154' is floriferous.
5. *Lavandula* 'Lavsts 154' exhibits light green foliage.

BRIEF DESCRIPTION OF THE DRAWINGS

The accompanying color drawings illustrate the overall appearance of the new cultivar 'Lavsts 154', showing colors as true as it is reasonably possible to obtain in colored reproductions of this type. Colors in the drawings may differ from the color values cited in the detailed botanical description, which accurately describe the actual colors of the new variety 'Lavsts 154'. The drawings are made from plants grown outside in Christchurch, New Zealand.

The drawing labeled as

The drawing labeled as

Figure 1:
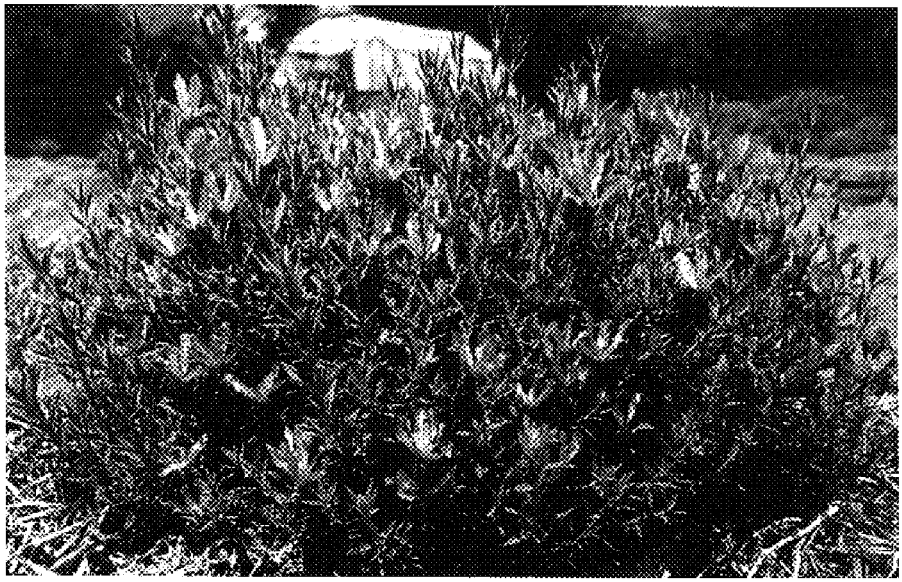
FIG. 1 shows an established plant, approximately two years old, growing in open ground and showing the habit of the entire plant.
Figure 2:
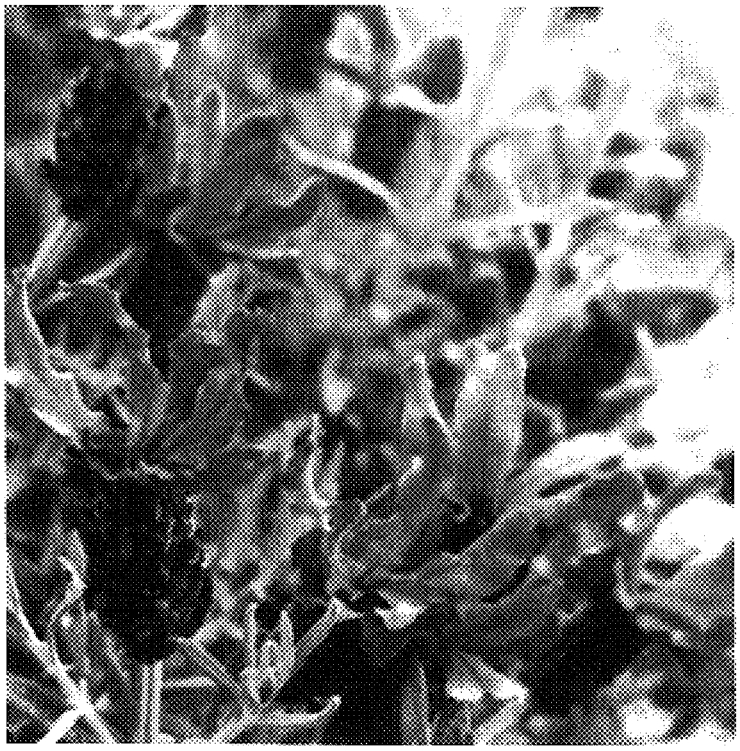

FIG. 2 illustrates the flower spikes and foliage of the instant plant, with approximately five or six sterile bracts.

The drawing labeled as

Figure 3:
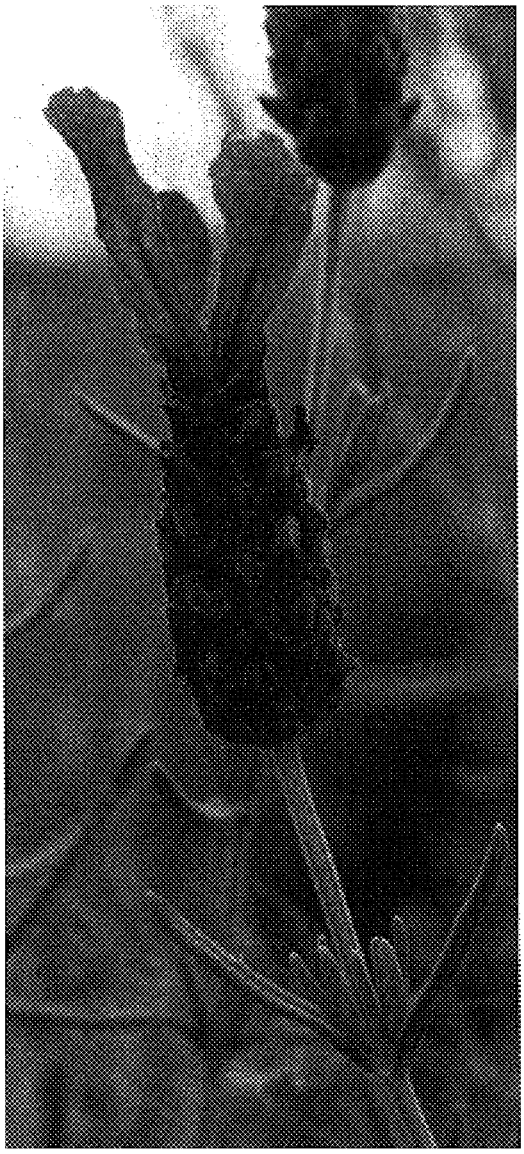

FIG. 3 illustrates the typical flower of the sport parent, 'Tickled Pink' (unpatented) with approximately four sterile bracts.

Both drawings are made using conventional photographic techniques and although colors may appear different from actual colors due to light reflectance, they are as accurate as possible by conventional photography.

BOTANICAL DESCRIPTION OF THE PLANT

The following is a detailed description of the *Lavandula* cultivar named 'Lavsts 154'. Data was collected in West Melton, Canterbury, New Zealand from plants grown in the open ground and in dry conditions. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. Color determination using The Royal Horticultural Society Colour Chart was conducted using the light box at The New Zealand Plant Variety Rights Office at Lincoln, Canterbury, New Zealand. Please note that the brown, green and violet range in this chart does not have an adequate color range to match that seen in lavender. The growing requirements are similar to the species and no disease problems have been observed.

Botanical classification: *Lavandula* 'Lavsts 154'.
Species: *Stoechas.*
Common name: Lavender.
Parentage: 'Lavasts 154' is a branch sport from the parent plant *Lavandula stoechas* subsp. *luisieri* 'Tickled Pink'.
Type: Aromatic perennial shrub.
Use: En masse, ornamental, hedge or potted plant.
Growth rate: Vigorous.
Habit: Upright bushy habit with erect, ascending flower spikes.
Plant height: 60–70 cm in height.
Plant width: 60–70 cm in width.
Hardiness: USDA Zones 5–8.
Disease resistance or susceptibility: No unusual or additional disease resistance or susceptibility compared to other cultivars of the species *Lavandula stoechas.*
Propagation method: Cuttings and tissue culture.
Root system: Fibrous.
Soil: Plant in well-drained soil.
Light levels: Plant in full sun.
Special needs: Prune after flowering to initiate second flowering period.
Time to initiate roots: 21 to 36 days are needed to develop roots on an unrooted cutting.
Time to develop to a one-gallon: 3 months are needed to produce a 1-gallon container plant from a rooted cutting.
Branching habit: Erect, upright and semi-open.
Seasonal interest: Flowers April–July and August.
Stem:
- *Shape.*—Square.
- *Surface.*—Puberulent.
- *Color.*—Both 144D (yellow-green) and 177B (brown) are present on the stems of an individual plant.
- *Size.*—3–5 mm in diameter.

Foliage:
- *Arrangement.*—Upright stems with whorls of leaves, arranged opposite along stem. A basal pair of leaves subtend each whorl of leaves. Dense arrangement of leaves along stems.
- *Leaf division.*—Simple.
- *Apices.*—Acute.
- *Base.*—Truncate to attenuate.
- *Margins.*—Entire and revolute.
- *Leaf shape.*—Linear.
- *Color of mature leaves* (*upper surface*).—138C.
- *Color of mature leaves* (*lower surface*).—138C.
- *Color of young leaves* (*upper surface*).—138C.
- *Color of young leaves* (*lower surface*).—Too revolute to view.
- *Upper and lower surfaces.*—Puberulent, older leaves more sparse covering.
- *Venation.*—Mid view depressed on upper surface and protruding beneath, side veins noticeable on lower surface.
- *Internodes.*—0.8–3 cm in length.
- *Foliar fragrance.*—Earthy pine scent.
- *Petiole.*—Basal leaves sessile, group leaves 0–0.3 cm.
- *Length.*—Approximately 0.8–2.5 cm in length.
- *Width.*—1–3 mm in width.

Flower spike:
- *Type of inflorescence.*—Terminal spike.
- *Size of inflorescence.*—2–5.5 cm in length and 1–1.3 cm in width.
- *Shape of inflorescence.*—Mostly cylindric or fusiform-conic with sterile bracts.
- *Peduncles.*—0.5–3.5 cm in height and 1–2 mm in width.
- *Peduncle color.*—144D (yellow-green).
- *Flower shape.*—Tubular.
- *Corolla.*—Two-lipped with upper lip 2-lobed and lower lip 3-lobed.
- *Corolla color.*—103A (dark blue).
- *Calyx color.*—Green or green with red-purple ribbing.
- *Calyx surface.*—Pubescent.
- *Bracteoles.*—None present.
- *Fertile bract shape.*—Cordate with acute apex.
- *Fertile bract color.*—Membranous with green veining, red-purple coloring around margins.
- *Fertile bract hair covering.*—Almost glabrous.
- *Sterile bract shape.*—Broadly obovate or spathulate.
- *Sterile bract margins.*—Moderately undulating.
- *Sterile bract length.*—15–25 mm.
- *Sterile bract colour.*—82C (vibrant pink-violet) to 87C (purple-violet).
- *Sterile bract number.*—5–6 sterile bracts per spike.
- *Fragrance.*—Camphoraceous.
- *Blooming period* (*New Zealand*).—October to February.
- *Blooming period* (*U.S.A.*).—April to August.

Reproductive organs:
- *Stamens.*—4.
- *Stamen length* (*2 posterior*).—1 mm.
- *Stamen length* (*2 anterior*).—1 mm.
- *Pistil.*—1.
- *Pistil length.*—4.5 mm.
- *Pistil diameter.*—Less than 0.25 mm.
- *Filament diameter.*—Less than 0.25 mm.
- *Filament color.*—Grayish-white.
- *Style length.*—3.5 mm.
- *Style color.*—Grayish-white.
- *Stigma shape.*—Oval.
- *Stigma color.*—Green.
- *Ovary shape.*—Globose.
- *Ovary dimensions.*—Too small to match, but approximately 0.5 mm long and 0.5 mm wide.
- *Ovary position.*—Superior.
- *Ovary color.*—Green.
- *Anther shape.*—Reniform.
- *Anther length.*—0.25 mm.
- *Anther color.*—Red-purple.
- *Pollen amount.*—Sparse.
- *Pollen color.*—Yellow.

Seed:
- *Number of seeds.*—4 seeds per calyx.
- *Colour of seeds.*—165A.
- *Length of seeds.*—1.5–2.5 mm. in length.

I claim:

1. A new and distinct variety of *Lavandula* plant named 'Lavsts 154' as described and illustrated.

* * * * *